US012576062B2

(12) United States Patent
Cuenoud

(10) Patent No.: US 12,576,062 B2
(45) Date of Patent: Mar. 17, 2026

(54) METHODS USING ADMINISTRATION OF MEDIUM CHAIN TRIGLYCERIDES (MCT) PRIOR TO A MEAL TO INCREASE KETONE PRODUCTION FROM THE MCTS

(71) Applicant: SOCIETE DES PRODUITS NESTLE S.A., Vevey (CH)

(72) Inventor: Bernard Cuenoud, Cully (CH)

(73) Assignee: Societe des Produits Nestle S.A., Vevey (CH)

( * ) Notice: Subject to any disclaimer, the term of this patent is extended or adjusted under 35 U.S.C. 154(b) by 829 days.

(21) Appl. No.: 17/440,021

(22) PCT Filed: Mar. 17, 2020

(86) PCT No.: PCT/EP2020/057315
§ 371 (c)(1),
(2) Date: Sep. 16, 2021

(87) PCT Pub. No.: WO2020/193291
PCT Pub. Date: Oct. 1, 2020

(65) Prior Publication Data
US 2022/0168256 A1 Jun. 2, 2022

Related U.S. Application Data

(60) Provisional application No. 62/822,299, filed on Mar. 22, 2019.

(51) Int. Cl.
| | |
|---|---|
| *A61K 31/23* | (2006.01) |
| *A61K 9/00* | (2006.01) |
| *A61P 3/00* | (2006.01) |

(52) U.S. Cl.
CPC ............ *A61K 31/23* (2013.01); *A61K 9/0053* (2013.01); *A61P 3/00* (2018.01)

(58) Field of Classification Search
CPC .............................. A61K 31/23; A61K 9/0053
See application file for complete search history.

(56) References Cited

U.S. PATENT DOCUMENTS

| | | | | |
|---|---|---|---|---|
| 11,000,496 | B2 * | 5/2021 | Cuenoud ................ | A61P 43/00 |
| 2004/0071751 | A1 | 4/2004 | Maki et al. | |
| 2004/0076719 | A1 | 4/2004 | Pimentel | |
| 2007/0179197 | A1 | 8/2007 | Henderson | |

FOREIGN PATENT DOCUMENTS

| | | |
|---|---|---|
| CN | 107921133 A | 4/2018 |
| CN | 108348496 A | 7/2018 |
| CN | 109069465 A | 12/2018 |
| CN | 110800904 | 2/2020 |
| CN | 113194733 A | 7/2021 |
| GB | 2568791 | 5/2019 |
| JP | 2009524587 A | 7/2009 |
| WO | 2009118968 | 10/2009 |
| WO | 2014153416 | 9/2014 |
| WO | 2018102914 A1 | 6/2018 |
| WO | 2018115158 | 6/2018 |

OTHER PUBLICATIONS

Courchesne-Loyer et al. "Emulsification increases the acute ketogenic effect and bioavailability of medium-chain triglycerides in humans" Current Developments in Nutrition, Jul. 1, 2017, vol. 1, No. 7, p. 1-32 (Year: 2017).*
Rolls et al. "Food intake in dieters and nondieters after a liquid meal containing medium-chain triglycerides" Am J Clin Nutr, 1988, vol. 48, pp. 66-71 (Year: 1988).*
Ota et al. "Effect of a ketogenic meal on cognitive function in elderly adults: potential for cognitive enhancement" Psychopharmacology, 2016, vol. 233, pp. 3797-3802 (Year: 2016).*
Vandenberghe et al., "Tricaprylin Alone Increases Plasma Ketone Response More Than Coconut Oil or Other Medium-Chain Triglycerides: An Acute Crossover Study in Healthy Adults", Current Developments in Nutrition, 2017, vol. 1, pp. 1-5 (Year: 2017).*
Strong First Forum, "MCT Oil: Best for Weight Loss", StrongFirst, Mar. 4, 2018, 19 pages (Year: 2018).*
Friedman et al., "Fuel partitioning and food intake: role for mitochondrial fatty acid transport", American Physiological Society, 1990, vol. 258, R216-R221 (Year: 1990).*
Phillips et al., "Spina Bifida Management", 2017, 47, pp. 173-177Curr Probl Pediatr Adolesc Health Care, 47, pp. 173-177 (Year: 2017).*
Phillips et al., "Spina Bifida Management", 2017, Curr Probl Pediatr Adolesc Health Care, 47, pp. 173-177 (Year: 2017).*
Gulati et al., "Cerebral Palsy: An Overview", 2018, Indian J Pediatr, 85, pp. 1006-1016 (Year: 2018).*
De Strooper et al., "The Cellular Phase of Alzheimer's Disease", 2016, Cell, 164, pp. 603-615 (Year: 2016).*
Scheltens et al., "Alzheimer's disease", 2016, The Lancet, 388, pp. 505-517 (Year: 2016).*

(Continued)

*Primary Examiner* — Brenda L Coleman
*Assistant Examiner* — Madeline E Braun
(74) *Attorney, Agent, or Firm* — K&L Gates LLP

(57) ABSTRACT

A method increases production of ketones derived from oral consumption of medium chain triglycerides (MCT) by an individual. The method includes orally administering to the individual a composition containing the MCTs and then subsequently orally administering to the individual a meal at least about ten minutes after the oral administration of the composition containing the MCTs and within about one hour of the oral administration of the composition containing the MCTs. For example, the meal can be administered about thirty minutes after the administration of the composition containing the MCTs. The ketone production is increased relative to ketone production from oral administration of the MCTs and the meal at approximately the same time. The meal can be breakfast. The composition containing the MCTs can be a liquid oral nutritional supplement (ONS) providing incomplete nutrition.

14 Claims, 1 Drawing Sheet

(56) References Cited

OTHER PUBLICATIONS

Chinese Office Action for Chinese Appl No. 202080017340.9 dated Apr. 24, 2024, 8 pages.

Chinese Office Action for Appl No. 202080017340.9 dated Jul. 19, 2023.

St-Onge et al. "Impact of medium and long chain triglycerides consumption on appetite and food intake in overweight men" European Journal of Clinical Nutrition, 2014, vol. 68, pp. 1134-1140.

Courchesne-Loyer et al. "Emulsification increases the acute ketogenic effect and bioavailability of medium-chain triglycerides in humans" Current Developments in Nutrition, Jul. 1, 2017, vol. 1, No. 7, 32 pages, XP55621372.

Otto et al. "Growth of human gastric cancer cells in nude mice is delayed by a ketogenic diet supplemented with omega-3 fatty acids and medium-chain triglycerides" BMC Cancer, 2008, vol. 8, No. 122, 12 pages.

Iemitsu et al. "The benefit of medium-chain triglyceride therapy on the cardiac function of SHRs is associated with a reversal of metabolic and signaling alterations" Am J Physiol Heart Circ Physiol, 2008, vol. 295, pp. H136-H144.

Maggio et al. "Food Intake After Intragastric Meals of Short-, Medium-, or Long-Chain Triglyceride" Physiology & Behavior, 1982, vol. 28, pp. 921-926.

Rizzo et al. "Coconut and sunflower oil ratios in ice cream influence subsequent food selection and intake" Physiology & Behavior, 2016, vol. 164, pp. 40-46.

Rolls et al. "Food intake in dieters and nondieters after a liquid meal containing medium-chain triglycerides" Am J Clin Nutr, 1988, vol. 48, pp. 66-71.

Marten et al. "Medium-chain triglycerides" International Dairy Journal, 2006, vol. 16, pp. 1374-1382.

Clegg "Medium-chain triglycerides are advantageous in promoting weight loss although not beneficial to exercise performance" International Journal of Food Sciences and Nutrition, 2010, vol. 61, No. 7, pp. 653-679.

Kinsella et al. "Coconut oil has less satiating properties than medium chain triglyceride oil" Physiology & Behavior, 2017, vol. 179, pp. 422-426.

Ota et al. "Effect of a ketogenic meal on cognitive function in elderly adults: potential for cognitive enhancement" Psychopharmacology, 2016, vol. 233, pp. 3797-3802.

Australian Office Action for Appl No. 2020246928 dated Oct. 31, 2024, 6 pages.

* cited by examiner

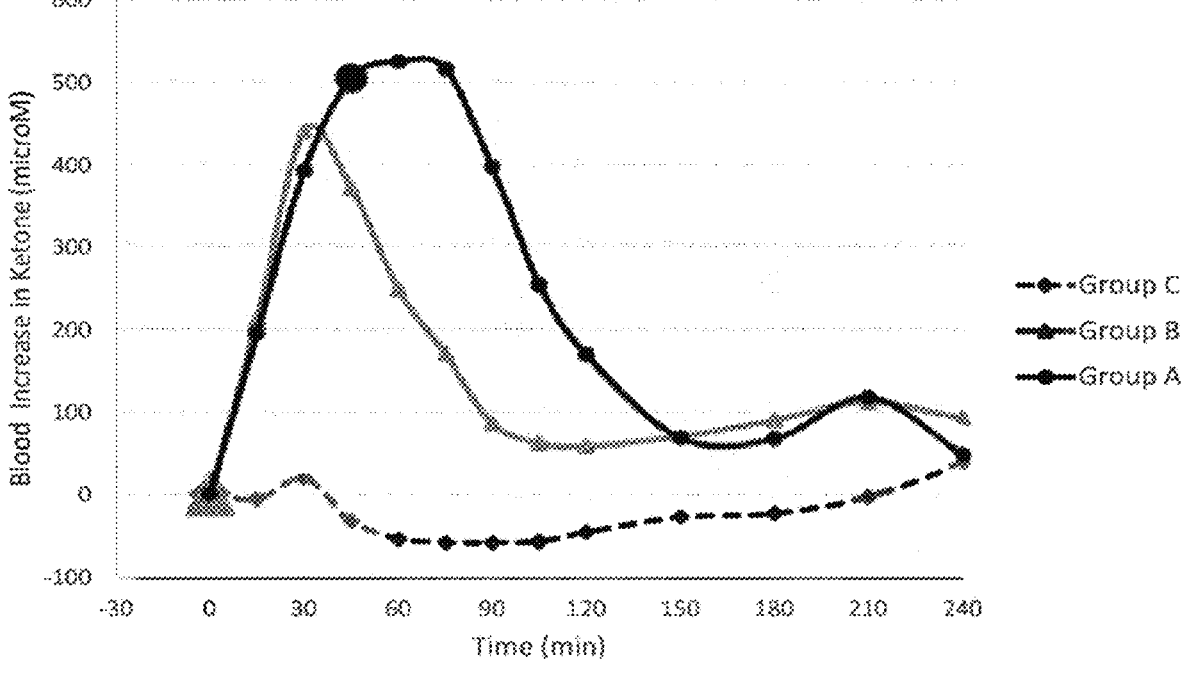

METHODS USING ADMINISTRATION OF MEDIUM CHAIN TRIGLYCERIDES (MCT) PRIOR TO A MEAL TO INCREASE KETONE PRODUCTION FROM THE MCTS

CROSS REFERENCE TO RELATED APPLICATIONS

The present application is a National Stage of International Application No. PCT/EP2020/057315, filed on Mar. 17, 2020, which claims priority to U.S. Provisional Patent Application No. 62/822,299, filed on Mar. 22, 2019, the entire contents of which are being incorporated herein by reference.

BACKGROUND

The present disclosure generally relates to administration of medium chain triglycerides (MCTs) before subsequent administration of a meal, for example administration of MCTs about thirty minutes before the meal.

The two main ketones, beta-hydroxybutyrate (BHB) and acteto-actetate (AcA), represent an important alternative source of energy for extrahepatic tissues like brain, heart or skeletal muscle. Moreover, accumulating evidence suggests that ketones might also have a signaling role, either direct or indirect. Products aimed at increasing blood ketones have potential therapeutic benefits in several conditions including epilepsy, neurological and neurodegenerative diseases, heart failure, diabetic cardiomyopathy, inborn errors of metabolism, obesity, type 2 diabetes, cancer, exercise performance, and nonalcoholic fatty liver disease (NAFLD) such as nonalcoholic steatohepatitis (NASH).

BHB and AcA are actively transported to the brain by the monocarboxylic transporter 1 (MCT1), resulting in brain levels directly proportional to their blood concentrations. Therefore, products that provide a higher and more sustained plasma level of ketones are anticipated to have a stronger and longer effect (higher area under the curve AUC) compared to products that raise blood ketones for a lower and shorter time span (smaller AUC). Hence it is critical to maximize the exposure to blood ketones. However, the factors that drive ketone plasma AUC derived from ketone precursors are not known.

Medium-chain triglycerides (MCTs) are efficient ketone precursors when administered by oral bolus. They are rapidly digested, and the resultant free medium chain fatty acids (MCFAs) are absorbed efficiently by the portal vein to reach the liver where they are extensively metabolized to ketones, bypassing the normal long-chain fatty acid digestion and absorption processes. Their specific formulation can affect ketogenesis efficiency and gastrointestinal tolerability.

Recently, human pharmacokinetic (PK) characterization of various MCT formulations has been reported, indicating that the intrinsic ketone production efficiency from MCT of various chain lengths varies, and a 8 carbon (C8) MCT being the most effective. Additionally, it was reported in humans that a good emulsion of the MCT oil displayed a much higher ketone production compared to the same non-emulsified oil after oral intake.

However, ketone production by oral intake of MCT is variable and not optimum. Moreover, intake of MCT without food often results in gastrointestinal (GI) side effects such as diarrhea.

SUMMARY

To the best knowledge of the present inventor, the impact of specific timing of a meal on the ketogenic effect of MCT has not been reported before the present patent application. As set forth in greater detail later herein, the inventors conducted a study that surprisingly and unexpectedly showed that an MCT emulsion administered prior to a meal provides the largest amount of blood ketones without GI side effects, compared to administration together with a meal, which both provided less amounts of blood ketones. Specifically, the relative timing of a meal strongly impacted ketone production from an MCT emulsion.

Accordingly, in a non-limiting embodiment, the present disclosure provides a method of increasing ketone production from medium chain triglycerides (MCT). The method comprises orally administering a composition comprising the MCTs to an individual and then subsequently orally administering a meal to the individual after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs. In an embodiment, the individual is elderly.

For example, the oral administration of the composition comprising the MCTs can be between about ten minutes before the administration of the meal and about one hour before the administration of the meal, preferably at least about fifteen minutes before the administration of the meal and within about forty minutes before the administration of the meal, most preferably about thirty minutes before the administration of the meal. Preferably the individual does not consume any food product other than optional water in a time period starting at the administration of the composition comprising the MCTs and ending at the administration of the meal.

The composition can be administered to the individual in a serving that provides up to about 30 g MCTs/serving, for example about 5 g to about 30 g MCTs/serving, about 10 g to about 30 g MCTs/serving, or about 15 g to about 30 g MCTs/serving. At least a portion of the MCTs can comprise at least one of octanoic acid or decanoic acid. At least a portion of the ketones produced from the MCTs can be selected from the group consisting of β-hydroxy butyrate, aceto-acetate and mixtures thereof.

In an embodiment, the ketone production achieved by the administration of the composition comprising the MCTs before the administration of the meal (e.g., administration of the MCTs about thirty minutes before the meal) is greater than ketone production from an identically formulated composition comprising MCTs administered at approximately the same time as the administration of the meal. The composition comprising the MCTs can be an oral nutritional supplement (ONS) that provides incomplete nutrition. Optionally the composition can comprise one or more ingredients additional to the MCTs, for example an optional additional component selected from the group consisting of a protein, a carbohydrate, a lipid, a vitamin, a mineral, an excipient, an emulsifier, a stabilizer, and mixtures thereof. The final formulation can be in a liquid format ready to consumed, or in a powder format to be reconstituted in water before use.

In another embodiment, the composition comprising the MCTs is used in a method of treating or preventing a condition for which increased ketone production from MCTs is beneficial. The method comprises orally administering a composition comprising the MCTs to an individual in need or at risk thereof and then subsequently orally administering a meal to the individual after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

In some embodiments, the composition comprising the MCTs is used to treat or prevent a condition selected from the group consisting of epilepsy, a neurological disease, a neurodegenerative disease, heart failure, diabetic cardiomyopathy, inborn errors of metabolism, obesity, types 2 diabetes, nonalcoholic fatty liver disease (NAFLD), nonalcoholic steatohepatitis (NASH), cancer, a brain energy deficiency condition, a migraine, a memory disorder, an age-related memory disorder, a brain injury, a stroke, amyloid lateral sclerosis, multiple sclerosis, cognitive impairment, cognitive impairment post-intensive care, age-induced cognition impairment, Alzheimer's disease, Parkinson's disease, Huntington's disease, an inherited metabolic disorder, bipolar disorder, schizophrenia, and combinations thereof.

In another embodiment, the composition comprising the MCTs is used in a method of improving or maintaining at least one of neurologic health, cognitive function, or exercise performance. The method comprises orally administering a composition comprising MCTs to an individual and then subsequently orally administering a meal to the individual after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

Additional features and advantages are described in, and will be apparent from, the following Detailed Description and the Figures.

BRIEF DESCRIPTION OF DRAWINGS

The Figure is a graph showing incremental mean total plasma ketones concentration over 4 hours from the metabolic study disclosed herein. Time 0 corresponds to the intake of the MCT product, and the large symbols correspond to timing of the breakfast intake.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

All percentages are by weight of the total weight of the composition unless expressed otherwise. Similarly, all ratios are by weight unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth. Ranges defined using "between" include the referenced endpoints.

As used herein and in the appended claims, the singular form of a word includes the plural, unless the context clearly dictates otherwise. Thus, the references "a," "an" and "the" are generally inclusive of the plurals of the respective terms. For example, reference to "an ingredient" or "a method" includes a plurality of such "ingredients" or "methods." The term "and/or" used in the context of "X and/or Y" should be interpreted as "X," or "Y," or "X and Y." Similarly, "at least one of X or Y" should be interpreted as "X," or "Y," or "both X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components. "Consisting essentially of" means that the embodiment or component thereof comprises more than 50 wt. % of the individually identified components, preferably at least 75 wt. % of the individually identified components, more preferably at least 85 wt. % of the individually identified components, most preferably at least 95 wt. % of the individually identified components, for example at least 99 wt. % of the individually identified components.

Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

"Animal" includes, but is not limited to, mammals, which includes but is not limited to rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage, e.g., an animal benefitting from ketones. While the term "individual" or "subject" is often used herein to refer to a human, the present disclosure is not so limited. Accordingly, the term "individual" or "subject" refers to any animal, mammal or human that can benefit from the methods and compositions disclosed herein.

The relative terms "improved," "increased," "enhanced" and the like refer to the effects of the method disclosed herein, particularly the administration of a composition containing MCTs before administration of a meal (e.g., about thirty minutes before the meal), relative to administration of an identically formulated composition containing MCTs but administered with a meal or after a meal (e.g., about thirty minutes after the meal). The terms "maintained" and "sustained" mean that a characteristic of an individual, such as neurologic health, cognitive function or exercise performance, is approximately the same as the average level for the preceding week, the average level for the preceding month, or the average level for the preceding year.

As used herein, the terms "treat" and "treatment" mean to administer a composition as disclosed herein to a subject having a condition in order to lessen, reduce or improve at least one symptom associated with the condition and/or to slow down, reduce or block the progression of the condition. The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The terms "prevent" and "prevention" mean to administer a composition as disclosed herein to a subject is not showing any symptoms of the condition to reduce or prevent development of at least one symptom associated with the condition. Furthermore, "prevention" includes reduction of risk, incidence and/or severity of a condition or disorder. As used herein, an "effective amount" is an amount that treats or prevents a deficiency, treats or prevents a disease or medical condition in an individual, or, more generally, reduces symptoms, manages progression of the disease, or provides a nutritional, physiological, or medical benefit to the individual.

As used herein, "administering" includes another person providing a referenced composition to an individual so that the individual can consume the composition and also includes merely the act of the individual themselves consuming a referenced composition.

The terms "food," "food product" and "food composition" mean a composition that is intended for ingestion by an individual, such as a human, and that provides at least one nutrient to the individual. "Food" and its related terms include any food, feed, snack, food supplement, treat, meal substitute, or meal replacement, whether intended for a human or an animal. Animal food includes food or feed intended for any domesticated or wild species. In preferred embodiments, a food for an animal represents a pelleted, extruded, or dry food, for example, extruded pet foods such as foods for dogs and cats.

The terms "serving" or "unit dosage form," as used herein, are interchangeable and refer to physically discrete units suitable as unitary dosages for human and animal subjects, each unit containing a predetermined quantity of the composition comprising MCTs disclosed herein in an amount sufficient to produce the desired effect, preferably in association with a pharmaceutically acceptable diluent, carrier or vehicle. The specifications for the unit dosage form depend on the particular compounds employed, the effect to be achieved, and the pharmacodynamics associated with each compound in the host. In an embodiment, the unit dosage form can be a predetermined amount of liquid housed within a container such as a bottle.

An "oral nutrition supplement" or "ONS" is a composition comprising at least one macronutrient and/or at least one micro nutrient, for example in a form of sterile liquids, semi-solids or powders, and intended to supplement other nutritional intake such as that from food. Non-limiting examples of commercially available ONS products include MERITENE®, BOOST®, NUTREN® and SUSTAGEN®. In some embodiments, an ONS can be a beverage in liquid form that can be consumed without further addition of liquid, for example an amount of the liquid that is one serving of the composition.

As used herein, "incomplete nutrition" refers to preferably nutritional products that do not contain sufficient levels of macronutrients (protein, fats and carbohydrates) or micronutrients to be sufficient to be a sole source of nutrition for the animal to which the nutritional product is being administered.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

A triglyceride (also known as a triacylglycerol or a triacylglyceride) is an ester that is derived from glycerol and three fatty acids. Fatty acids may be either unsaturated or saturated. Fatty acids which are not attached to other molecules are referred to as free fatty acids (FFA).

A medium-chain triglyceride (MCT) is a triglyceride in which all three fatty acid moieties are medium-chain fatty acid moieties. As defined herein, medium-chain fatty acids (MCFA) are fatty acids that have 6 to 12 carbon atoms. Medium-chain fatty acids with 8 carbon atoms may be referred to herein as "C8 fatty acids" or "C8." Medium-chain fatty acids with 10 carbon atoms may be referred to herein as "C10 fatty acids" or "C10."

The term "fatty acid moiety" refers to the part of the MCT that originates from a fatty acid in an esterification reaction with glycerol. In a non-limiting example, an esterification reaction between glycerol and only octanoic acid would result in a MCT with octanoic acid moieties. In another non-limiting example, an esterification reaction between glycerol and only decanoic acid would result in a MCT with decanoic acid moieties.

Octanoic acid (also known as caprylic acid) is a saturated fatty acid of the formula $CH_3(CH_2)_6COOH$.

Decanoic acid (also known as capric acid) is a saturated fatty acid of the formula $CH_3(CH_2)_8COOH$.

Embodiments

An aspect of the present disclosure is a method of increasing ketone production from medium chain triglycerides (MCTs). The method comprises orally administering a composition comprising the MCTs to an individual and then subsequently orally administering a meal to the individual after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs. As used herein, "subsequently" means at least about five minutes later, preferably ten minutes later, more preferably at least about fifteen minutes later, even more preferably at least about twenty minutes later, yet more preferably at least about twenty-five minutes later, most preferably about thirty minutes later.

As used herein, "meal" refers to one or more food products consumed at substantially the same time as each other; preferably such that at least one macronutrient and at least one micronutrient are provided by consuming the meal; more preferably such that one or more proteins, one or more carbohydrates, one or more fats, one or more vitamins and one or more minerals are provided by consuming the meal. Preferably the meal comprises a plurality of food products. In an embodiment, the meal provides 200 kcal to 1,000 kcal to the individual, preferably 250 kcal to 900 kcal, more preferably 300 kcal to 850 kcal, and most preferably 350 kcal to 800 kcal. In an embodiment, the meal is substantially free of MCTs (i.e., less than 2.5 wt. %, preferably less than 2.0 wt. %, more preferably less than 1.0 wt. %, most preferably less than 0.5 wt. % MCTs) or completely free of MCTs.

The administration of the composition comprising the MCTs can be between about ten minutes before the administration of the meal and about one hour before the administration of the meal, preferably between about fifteen minutes before the administration of the meal and about forty minutes before the administration of the meal, such as about thirty minutes before the administration of the meal. Preferably the individual does not consume any food product other than optional water in the time period between the administration of the composition comprising the MCTs and the administration of the meal.

In some embodiments, the meal is breakfast. For example, the composition comprising the MCTs can be administered to the individual before breakfast, and then the breakfast can be subsequently administered to the individual after the administration of the composition comprising MCTs. For example, the breakfast can be administered between about ten minutes after the administration of the composition comprising MCTs and about one hour after the administration of the composition comprising MCTs, preferably at least about fifteen minutes after the oral administration of the composition comprising the MCTs and within about forty minutes after the oral administration of the composition comprising the MCTs, most preferably about thirty minutes after the administration of the composition comprising MCTs.

As used herein, "breakfast" is the first meal consumed by the individual on the particular day. For example, breakfast can be consumed before noon according to the local time of the individual, preferably before 11:00 AM according to the local time of the individual, more preferably before 10:00 AM according to the local time of the individual, most preferably before 9:00 AM according to the local time of the individual, but after the individual has awakened from sleep and/or after 4:00 AM according to the local time of the individual, preferably after 5:00 AM according to the local time of the individual, more preferably after 6:00 AM according to the local time of the individual, most preferably after 7:00 AM according to the local time of the individual.

In an embodiment, the composition is administered to an individual in a serving that provides at least about 5 g MCTs, for example at least about 10 g MCTs, such as at least about 15 g MCTs. In some embodiments, up to 30 g MCTs are administered per serving of the composition.

The MCTs comprise three fatty acid moieties, each of which independently has between 6-12, 6-11, 6-10, 7-12, 7-11, 7-10, 8-12, 8-11 or 8-10 carbon atoms. In an embodiment, at least a portion of the MCTs contain one or more octanoic acid moieties. In an embodiment, at least a portion of the MCTs contain one or more decanoic acid moieties.

Preferably the composition contains one or more natural sources that provide at least a portion of the MCTs. Non-limiting examples of suitable natural sources of MCTs include plant sources such as coconuts, coconut oil, palm kernels, and palm kernel oils, and also include animal sources such as milk. For example, decanoic acid and octanoic acid form about 5-8% and 4-10% of the fatty acid composition of coconut oil, respectively.

Additionally or alternatively, at least a portion of the MCTs may be synthesized by esterification of glycerol with one or more medium-chain fatty acids (MCFA) with a tail of 6 to 12 carbon atoms. For example, a homotriglyceride comprising three fatty acid moieties each with 8 carbon atoms can be synthesized by esterification of glycerol with C8 fatty acids (e.g., octanoic acid), and a homotriglyceride comprising three fatty acid moieties each with 10 carbon atoms can be synthesized by esterification of glycerol with C10 fatty acids (e.g., decanoic acid).

In an embodiment, the composition comprises MCTs comprising at least one octanoic acid moiety or decanoic acid moiety, and the composition is free from or substantially free from any other triglycerides. As used herein, the term "free from any other triglycerides" means that the composition does not comprise any triglycerides that do not contain at least one octanoic acid moiety or decanoic acid moiety. As used herein, the term "substantially free from any other triglycerides" means that the composition may contain traces of other triglycerides, i.e., less than 5 mol %, preferably less than 3 mol %, more preferably less than 2 mol %, even more preferably less than 1 mol % or most preferably less than 0.5 mol %.

In some embodiments, the composition comprising MCTs may be in the form of a nutritional composition or a nutritional supplement. The term "nutritional supplement" refers to a product which is intended to supplement the general diet of a subject. For example, the composition comprising the MCTs can be an oral nutritional supplement (ONS) that provides incomplete nutrition. Nevertheless, the ONS can comprise one or more ingredients additional to MCTs, for example an additional component selected from the group consisting of a protein, a carbohydrate, a lipid, a vitamin, a mineral, and mixtures thereof. Moreover, in an alternative embodiment, the composition comprising the MCTs may be in the form of a complete nutritional product. The term "complete nutritional product" refers to a product which is capable of being the sole source of nutrition for the subject.

In a preferred embodiment, the composition comprises the MCTs emulsified in a mixture of one or more of protein, lipid or carbohydrate and optionally further comprises a dietary flavoring (e.g., vanilla).

Non-limiting examples of suitable proteins include animal proteins, such as milk protein, meat protein and egg protein; or vegetable proteins, such as soy protein, wheat protein, rice protein, pea protein, corn protein, canola protein, oat protein, potato protein, peanut protein, and any proteins derived from beans, buckwheat or lentils. Milk proteins, such as casein and whey, and soy proteins may be preferred for some applications. If the protein is a milk protein or a milk protein fraction, the protein may be, for example, sweet whey, acid whey, $\alpha$-lactalbumin, $\beta$-lactoglobulin, bovine serum albumin, acid casein, caseinates, $\alpha$-casein, $\beta$-casein and/or $\gamma$-casein.

Non-limiting examples of suitable carbohydrates include mono-saccharides and/or di-saccharides, slowly digested fully caloric carbohydrates, oligosaccharides, or mixtures thereof. Particular non-limiting examples include maltodextrin, maltose, high-maltose corn syrup, fructose, galactose, sucrose, lactose or a mixture of thereof.

Non-limiting examples of suitable lipids additional to the MCTs include monoacylglycerols (MAG), diacylglycerol (DAG), long chain triglycerides (LCT), short chain fatty acids (SCFA), branched chain fatty acids (BCFA), structured MAG, structured DAG, fatty acids (free and/or bound, e.g., esterified to glycerol or as ethyl esters), phospholipids, lyso-phospholipids, sphingomyelin, gangliosides, specialized pro-resolving mediators (SPMs), or mixtures thereof. The fatty acids that are free and/or bound may include one or more of linoleic acid (18:2n-6), alpha-linolenic acid (18:3n-3), dihomogammalinolenic acid (20:3n-6), gamma-linolenic acid (GLA, 18:3n-6), stearidonic acid (18:4n-3), docosapentaenoic acid (DPA, 22:5n-3) or mixtures thereof. The source of the lipids may be one or more of animal, plant, fermented, microalgae, GMO, non-GMO or mixtures thereof.

An embodiment of the composition comprising the MCTs is a non-complete liquid ONS that can further comprise protein, e.g., milk protein concentrate. In an embodiment of this non-complete liquid ONS, the composition can consist essentially of water, the MCTs and the protein (e.g., milk protein concentrate) and optionally a flavoring. Preferably the non-complete liquid ONS is a "shot," for example having a volume of about 40 mL to about 400 mL, more preferably about 50 mL to about 300 mL, most preferably about 70 mL. Preferably the non-complete liquid ONS is in a unit dosage form that provides at least about 5 g MCTs, more preferably at least about 10 g MCTs, most preferably at least about 15 g MCTs, and in some embodiments, no greater than 30 g MCTs. In a particularly preferred embodiment, the non-complete liquid ONS is an MCT emulsion.

The proteins can be 0 wt. % to about 50 wt. % of the composition, preferably about 0.1 wt. % to about 20 wt. % of the composition, more preferably about 1.0 wt. % to about 10.0 wt. % of the composition, most preferably about 5.0 wt. % of the composition. The proteins can be 0 g to about 30 g/serving of the composition, preferably about 5 g to about 30 g/serving of the composition.

Another embodiment of the composition comprising the MCTs is a complete liquid meal replacement that can further comprise protein (e.g., one or more of whey, casein, milk protein concentrate), additional lipid (e.g., long chain triglycerides (LCT)) and carbohydrate (lactose and/or glucose).

In an embodiment of this complete liquid meal replacement, the composition can consist essentially of water, the MCTs the protein, the additional lipid, the carbohydrates, and optionally a flavoring. Preferably the complete liquid meal replacement is a "shot," for example having a volume of about 40 mL to about 400 mL, more preferably about 50 mL to about 300 mL, most preferably about 70 mL. Preferably the complete liquid meal replacement is in a unit dosage form that provides at least about 5 g MCTs, more preferably at least about 10 g MCTs, most preferably at least about 15 g MCTs, and in some embodiments, no greater than 30 g MCTs. In a particularly preferred embodiment, the complete liquid meal replacement is an MCT emulsion.

The format of the MCT product can contain excipients, emulsifiers, stabilzers and mixtures thereof, and the final formulation can be in a liquid or gel format ready to be consumed, or in a powder format to be reconstituted in water before use.

The MCTs can be about 10 to about 120 g/L of the composition. The proteins can be 0 to about 200 g/L of the composition, preferably about 10 g/L to about 200 g/L of the composition. The additional lipids can be 0 to about 120 g/L of the composition, preferably about 10 g/L to about 200 g/L of the composition. The carbohydrates can be 0 to about 200 g/L of the composition, preferably about 10 g/L to about 200 g/L of the composition.

In some embodiments, the composition comprising the MCTs is provided in a kit also providing at least a portion of the meal. For example, the composition comprising the MCTs and at least a portion of the meal can be provided in separate containers relative to each other but both housed within a larger container.

After oral absorption, MCTs are metabolized to free fatty acids and further metabolized to ketones. The free fatty acids are initially metabolized to $\beta$-hydroxy butyrate (BHB) and then aceto acetate (AcA). MCFA and ketones can be produced in various amounts in bodily fluids depending on the MCT utilized, and they may be used as an alternative source of energy to glucose or to supplement the energy derived from glucose.

Ketones can be transported to the brain by, for example, monocarboxylic transporter 1 (MCT1) where they are mainly metabolized by neurons. Free fatty acids, such as C8 free fatty acids and C10 free fatty acids, can reach the brain by diffusion where they are mainly metabolized by astrocytes.

In an embodiment, oral administration of the composition to the subject provides one or more of ketones, C8 fatty acids, or C10 fatty acids to a bodily fluid of that subject. Preferably, the ketones are $\beta$-hydroxy butyrate and/or aceto acetate. In an embodiment, the ketone production achieved by the administration of the composition comprising the MCTs before the meal (e.g., about thirty minutes before the meal) is greater than ketone production from an identically formulated composition comprising MCTs administered at approximately the same time as the meal. The exposure of the subject to ketones can be quantified by measuring the levels of ketones in the subject's plasma, e.g., over 4 hours following oral administration. The exposure of a subject to a ketone may be calculated by determining the area under the curve (AUC) in a plot of concentration of ketone in a bodily fluid e.g., blood plasma, against time (e.g., over 4). In an embodiment, biological fluids are treated prior to analysis with organic solvent to precipitate protein and reconstituted in a enzymatic assay or mass spectrometry (MS) compatible solvent. Levels of ketone bodies can be assessed using standard enzymatic assays or liquid chromatography coupled to high resolution mass spectrometry (LC-MS). In particular, β-hydroxy butyrate (BHB) and aceto acetate (AcA) concentrations can be quantitatively measured using an external calibration methodology.

The composition comprising the MCTs may further comprise one or more additional components such as minerals; vitamins; salts; or functional additives including, for example, palatants, colorants, emulsifiers, antimicrobial or other preservatives. Non-limiting examples of suitable minerals for the compositions disclosed herein include calcium, phosphorous, potassium, sodium, iron, chloride, boron, copper, zinc, magnesium, manganese, iodine, selenium, chromium, molybdenum, fluoride and any combination thereof. Non-limiting examples of suitable vitamins for the compositions disclosed herein include water-soluble vitamins (such as thiamin (vitamin B1), riboflavin (vitamin B2), niacin (vitamin B3), pantothenic acid (vitamin B5), pyridoxine (vitamin B6), biotin (vitamin B7), myo-inositol (vitamin B8) folic acid (vitamin B9), cobalamin (vitamin B12), and vitamin C) and fat-soluble vitamins (such as vitamin A, vitamin D, vitamin E, and vitamin K) including salts, esters or derivatives thereof. Inulin, taurine, carnitine, amino acids, enzymes, coenzymes, and any combination thereof may be included in various embodiments.

The composition may further comprise one or more agents that promote or sustain general neurologic health or further enhance cognitive function. Examples of such agents include choline, phosphatidylserine, alpha-lipoic acid, CoQ10, acetyl-L-carintine, herbal extracts (such as Gingko biloba, Bacopa monniera, Convolvulus pluricaulis and Leucojum aestivum), omega-3 or omega-6 polyunsaturated fatty acids (such as eicosapentaenoic acid, docosapentaenoic acid or docosahexaenoic acid as free fatty acid), aliphatic ester (such as ethylester, triglycerides or monoglycerides formats), and fish oil extracts.

The subject may be a mammal such as a human, canine, feline, equine, caprine, bovine, ovine, porcine, cervine or a primate. Preferably the subject is a human. In an embodiment, the subject is an infant. The infant may, for example, be a human such as a newborn infant (i.e., a baby under 28 days of age) or a premature infant (i.e., a baby born before 37 completed weeks of gestation).

In an embodiment, the subject is an aging subject. For instance, a subject may be an aging subject when it has reached 40, 50, 60, 66, 70, 75, or 80% of its likely lifespan. A determination of lifespan may be based on actuarial tables, calculations, or estimates, and may consider past, present, and future influences or factors that are known to positively or negatively affect lifespan. Consideration of species, gender, size, genetic factors, environmental factors and stressors, present and past health status, past and present nutritional status, and stressors may be taken into consideration when determining lifespan. The aging subject may, for example, be a human subject over the age of 40, 45, 50, 55, 60, 65, 70, 75, 80, 85, 90, 95 or 100 years old.

Further in this regard, the term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

All references herein to treatment include curative, palliative and prophylactic treatment. Treatment may also include arresting progression in the severity of a disease. Both human and veterinary treatments are within the scope of the present disclosure. Preferably the composition comprising the MCTs is administered in a serving or unit dosage form that provides a therapeutically effective or prophylactically effective amount of the MCTs and/or provides an amount of MCTs metabolized into a therapeutically effective or prophylactically effective amount of ketones.

Free fatty acids and ketones produced from MCTs can provide an alternative energy source to glucose to supplement or replace the energy in cells such as astrocytes, myocytes, cardiomyocytes, or neuronal cells.

Brain tissue consumes a large amount of energy in proportion to its volume. In an average healthy subject, the brain obtains most of its energy from oxygen-dependent metabolism of glucose. Typically, the majority of the brain's energy is used to help neurons or nerve cells send signals and the remaining energy is used for cell-health maintenance. A deficiency in brain energy, for example caused by impairment of glucose utilisation, can result in neuronal hyperactivity, seizures and cognitive impairments.

Examples of brain energy deficiency conditions or diseases include: migraine, memory disorder, age-related memory disorder, brain injury, neurorehabilitation, stroke and post-stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

As used herein, the term "neurological condition" refers to a disorder of the nervous system. Neurological conditions may result from damage to the brain, spinal column or nerves, caused by illness or injury. Non-limiting examples of the symptoms of a neurological condition include paralysis, muscle weakness, poor coordination, loss of sensation, seizures, confusion, pain and altered levels of consciousness. An assessment of the response to touch, pressure, vibration, limb position, heat, cold, and pain as well as reflexes can be performed to determine whether the nervous system is impaired in a subject.

Some neurological conditions are life-long, and the onset can be experienced at any time. Other neurological conditions, such as cerebral palsy, are present from birth. Some neurological conditions, such as Duchenne muscular dystrophy, commonly appear in early childhood, while other neurological conditions, such as Alzheimer's disease and Parkinson's disease, affect mainly older people. Some neurological conditions have a sudden onset due to injury or illness, such as a head injury or stroke, or cancers of the brain and spine.

In an embodiment, the neurological condition is the result of traumatic damage to the brain. Additionally or alternatively, the neurological condition is the result of an energy deficiency in the brain or in the muscles.

Examples of neurological conditions include migraine, memory disorder, age-related memory disorder, brain injury, neurorehabilitation, stroke and post-stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

A migraine is an intense headache accompanied by other symptoms such as nausea (feeling sick), visual problems and an increased sensitivity to light or sound. A migraine may be preceded by an aura; the main symptoms of an aura are visual problems such as blurred vision (difficulty focusing), blind spots, flashes of light, or a zigzag pattern moving from the central field of vision towards the edge.

Strokes (also known as cerebrovascular accident (CVA) and cerebrovascular insult (CVI)) occur when there is poor blood flow to the brain resulting in cell death. There are two main types of stroke: ischemic (due to lack of blood flow) and haemorrhagic (due to bleeding). Strokes result in part of the brain not functioning properly. The signs and symptoms of a stroke may include an inability to move or feel on one side of the body, problems understanding or speaking, feeling like the world is spinning, or loss of vision to one side. The signs and symptoms often appear soon after the stroke has occurred.

Amyotrophic lateral sclerosis (ALS) (also known as Lou Gehrig's disease, Charcot disease and motor neuron disease), involves the death of neurons responsible for controlling voluntary muscles. ALS is characterized by stiff muscles, muscle twitching, and gradually worsening weakness due to muscle wasting; this results in difficulty speaking, swallowing, and eventually breathing.

Multiple sclerosis affects the nerves in the brain and spinal cord, causing a wide range of symptoms including problems with muscle movement, problems with mobility and balance, numbness and tingling, blurring of vision (typically there is loss of vision in one eye) and fatigue.

Parkinson's disease is a degenerative disorder of the central nervous system mainly affecting the motor system. In the early course of the disease, the most obvious symptoms are movement-related; these include tremor at rest, rigidity, slowness of movement and difficulty with walking and gait. Later in the course of the disease, thinking and behavioral problems may arise, with dementia commonly occurring in the advanced stages of the disease. Other symptoms include depression, sensory, sleep and emotional problems.

Alzheimer's disease is a progressive neurodegenerative disorder. Alzheimer's disease is the most common cause of dementia. Symptoms include memory loss and difficulties with thinking, problem-solving or language. The mini mental state examination (MMSE) is an example of one of the tests used to diagnose Alzheimer's disease.

Huntington's disease is an inherited condition that damages certain nerve cells in the brain. Huntington's disease affects muscle coordination and leads to mental decline and behavioral symptoms. The earliest symptoms are often subtle problems with mood or cognition. A general lack of coordination and an unsteady gait often follow. As the disease advances, uncoordinated, jerky body movements become more apparent, along with a decline in mental abilities and behavioral symptoms. Physical abilities gradually worsen until coordinated movement becomes difficult. Mental abilities generally decline into dementia.

Inherited metabolic disorders are a range of diseases caused by defective genes. Typically the defective gene(s) results in a defect in an enzyme or in a transport protein which results in a block in the way that a compound is processed by the body such that there is a toxic accumulation of the compound. Inherited metabolic disorders can affect any organ and usually affect more than one. Symptoms often tend to be nonspecific and usually relate to major organ dysfunction or failure. The onset and severity of a metabolic disorder may be exacerbated by environmental factors, such as diet and concurrent illness.

Glucose transporter type 1 (Glut1) deficiency syndrome is a genetic metabolic disorder involving the GLUT1 protein which transports glucose across the blood-brain barrier or the boundary separating tiny blood vessels from brain tissue.

The most common symptom is seizures (epilepsy), which usually begin within the first few months of life. Additional symptoms that can occur include varying degrees of cognitive impairment and movement disorders characterized by ataxia, dystonia, and chorea. Glut1 deficiency syndrome may be caused by mutations in the SLC2A1 gene which produce GLUT1 protein.

Pyruvate dehydrogenase complex deficiency (pyruvate dehydrogenase deficiency or PDCD) is a neurodegenerative disorder associated with abnormal mitochondrial metabolism and disrupted carbohydrate metabolism. PDCD is characterized by the buildup of lactic acid in the body and a variety of neurological problems. Signs and symptoms of this condition usually first appear shortly after birth, and they can vary widely among affected individuals. The most common feature is a potentially life-threatening buildup of lactic acid (lactic acidosis), which can cause nausea, vomiting, severe breathing problems, and an abnormal heartbeat. Other symptoms include: neurological problems; delayed development of mental abilities and motor skills such as sitting and walking; intellectual disability; seizures; weak muscle tone (hypotonia); poor coordination, and difficulty walking. Some affected individuals have abnormal brain structures, such as underdevelopment of the tissue connecting the left and right halves of the brain (corpus callosum), wasting away (atrophy) of the exterior part of the brain known as the cerebral cortex, or patches of damaged tissue (lesions) on some parts of the brain.

PDCD is a deficiency of one of the proteins in the pyruvate dehydrogenase complex (PDC). The pyruvate dehydrogenase complex comprises three enzymes identified as E1, E2 and E3; the E1 enzyme contains subunits identified as alpha and beta. The most common form of PDCD is caused by an abnormal gene in the E1 alpha subunit (the PDHA1 gene) located on the X chromosome. Some PDCD cases are caused by a mutation in a gene in another subunit of the pyruvate dehydrogenase complex such as the PDHX gene, the PDHB gene, the DLAT gene, the PDP1 gene, and the DLD gene.

Bipolar disorder is a brain disorder that causes unusual shifts in mood, energy, activity levels, and the ability to carry out day-to-day tasks. Bipolar disorder is characterized by periods of elevated mood and periods of depression. Bipolar disorder can be diagnosed using the guidelines from the Diagnostic and Statistical Manual of Mental Disorders (DSM) or the World Health Organization's International Statistical Classification of Diseases and Related Health Problems.

Schizophrenia is a chronic, severe, and disabling brain disorder in which individuals interpret reality abnormally. Schizophrenia may result in some combination of hallucinations, hearing voices, delusions, and extremely disordered thinking and behavior. Schizophrenia can be diagnosed using the guidelines from the Diagnostic and Statistical Manual of Mental Disorders (DSM) or the World Health Organization's International Statistical Classification of Diseases and Related Health Problems.

Epilepsy is a neurological disorder in which nerve cell activity in the brain becomes disrupted, causing seizures or periods of unusual behavior, sensations and sometimes loss of consciousness.

Diabetic cardiomyopathy (DCM) is a disorder of the heart muscle in people with diabetes. It can lead to inability of the heart to circulate blood through the body effectively, a state known as heart failure, with accumulation of fluid in the lungs or legs.

The terms "cognitive impairment" and "cognition impairment" refer to disorders that give rise to impaired cognition, in particular disorders that primarily affect learning, memory, perception, and/or problem solving.

Cognitive impairment may occur in a subject after intensive care. Cognitive impairment may occur as part of the ageing process.

The term "cognition" refers to the set of all mental abilities and processes, including knowledge, attention, memory and working memory, judgment and evaluation, reasoning and "computation", problem solving and decision making, comprehension and production of language. Levels of and improvements in cognition can be readily assessed by the skilled person using any suitable neurological and cognitive tests that are known in the art, including cognitive tests designed to assess speed of information processing, executive function and memory. Suitable example tests include Mini Mental State Examination (MMSE), Cambridge Neuropsychological Test Automated Battery (CANTAB), Alzheimer's Disease Assessment Scale-cognitive test (ADAScog), Wisconsin Card Sorting Test, Verbal and Figural Fluency Test and Trail Making Test, Wechsler Memory scale (WMS), immediate and delayed Visual Reproduction Test (Trahan et al. Neuropsychology, 1988 19(3) p. 173-89), the Rey Auditory Verbal Learning Test (RAVLT) (Ivnik, R J. et al. Psychological Assessment: A Journal of Consulting and Clinical Psychology, 1990 (2): p. 304-312), electroencephalography (EEG), magnetoencephalography (MEG), Positron Emission Tomography (PET), Single Photon Emission Computed Tomography (SPECT), Magnetic Resonance Imaging (MRI), functional Magnetic Resonance Imaging (fMRI), computerized tomography and long-term potentiation.

EEG, a measure of electrical activity of the brain, is accomplished by placing electrodes on the scalp at various landmarks and recording greatly amplified brain signals. MEG is similar to EEG in that it measures the magnetic fields that are linked to electrical fields. MEG is used to measure spontaneous brain activity, including synchronous waves in the nervous system.

PET provides a measure of oxygen utilisation and glucose metabolism. In this technique, a radioactive positron-emitting tracer is administered, and tracer uptake by the brain is correlated with brain activity. These tracers emit gamma rays which are detected by sensors surrounding the head, resulting in a 3D map of brain activation. As soon as the tracer is taken up by the brain, the detected radioactivity occurs as a function of regional cerebral blood flow. During activation, an increase in cerebral blood flow and neuronal glucose metabolism can be detected within seconds.

Suitable analysis can also be based on neuropsychiatric testing, clinical examinations and individual complaints of loss of cognitive function (e.g. subjective memory loss). Further suitable tests may be based on assessments of locomotion, memory and attention, seizure susceptibility, and social interaction and/or recognition.

Memory disorders are the result of neurological damage to the brain structures such that the storage, retention and recollection of memories are hindered. Memory disorders can be progressive with age (e.g. Alzheimer's disease), or they can be immediately resulting, for example, from a head injury. Levels of and improvements in memory disorders can be readily assessed by the skilled person using any suitable tests that are known in the art such as Alzheimer's Disease Assessment Scale-cognitive test (ADAScog), Mini Mental State Examination (MMSE), computerized tomography (CT) scan, Magnetic Resonance Imaging (MRI), Single Photon Emission Computed Tomography (SPECT), Positron Emission Tomography (PET), and electroencephalography (EEG).

In view of the above disclosures, an embodiment provided herein is a method of increasing production of ketones derived from oral consumption of medium chain triglycerides (MCT) by an individual, the method comprising: orally administering to the individual a composition comprising the MCTs; and subsequently orally administering to the individual a meal after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

The production of the ketones in the individual is preferably increased relative to ketone production from oral administration of the composition comprising the MCTs and the meal to the individual at approximately the same time.

The individual can be elderly. The composition comprising the MCTs can be a liquid. The composition can be administered to the individual in a serving comprising at least about 15.0 g of the MCTs up to about 30.0 g of the MCTs. The composition can comprise the MCTs emulsified in at least one additional component selected from the group consisting of a protein, a lipid and a carbohydrate.

At least a portion of the MCTs can be at least one of octanoic acid or decanoic acid. At least a portion of the ketones can be selected from the group consisting of β-hydroxy butyrate, acetone-acetate and mixtures thereof.

The meal can be breakfast. The composition can be a liquid incomplete nutrition oral nutritional supplement (ONS).

Preferably, the individual does not experience gastrointestinal side effects from the MCTs. Preferably, the individual does not consume any food products other than optional water during a time period starting at the oral administration of the composition comprising the MCTs to the individual and ending at the oral administration of the meal to the individual.

Another embodiment provided herein is a method of treating or preventing a condition for which increased production of ketones from medium chain triglycerides (MCTs) is beneficial, the method comprising: orally administering to an individual in need thereof or at risk thereof a composition comprising the MCTs; and subsequently orally administering to the individual a meal after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

The condition can be selected from the group consisting of epilepsy, a neurological disease, a neurodegenerative disease, heart failure, inborn errors of metabolism, obesity, types 2 diabetes, nonalcoholic fatty liver disease (NAFLD), nonalcoholic steatohepatitis (NASH), cancer, a brain energy deficiency condition, a migraine, a memory disorder, an age-related memory disorder, a brain injury, a stroke, amyloid lateral sclerosis, multiple sclerosis, cognitive impairment, cognitive impairment post-intensive care, age-induced cognition impairment, Alzheimer's disease, Parkinson's disease, Huntingdon's disease, an inherited metabolic disorder, bipolar disorder, schizophrenia, and combinations thereof.

Another embodiment provided herein is a method of improving or maintaining at least one of neurologic health, cognitive function, or exercise performance, the method comprising: orally administering to the individual a composition comprising medium chain triglycerides (MCTs); and subsequently orally administering to the individual a meal after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

Another embodiment provided herein is a kit for providing nutrition, the kit comprising: an orally administrable composition comprising the MCTs; at least a portion of a meal, stored separately in the kit from the orally administrable composition comprising the MCTs; and instructions to orally administer to an individual a composition comprising medium chain triglycerides (MCTs) and then subsequently orally administer to the individual a meal after the oral administration of the composition comprising the MCTs and within about one hour of the oral administration of the composition comprising the MCTs, for example at least about ten minutes after the oral administration of the composition comprising the MCTs and within about on hour after the oral administration of the composition comprising the MCTs, preferably at least about fifteen minutes after the oral administration of the composition comprising the MCTs and within about forty minutes after the oral administration of the composition comprising the MCTs, most preferably about thirty minutes after the oral administration of the composition comprising the MCTs.

Example

The following non-limiting example presents clinical data developing and supporting the concepts of the present disclosure.

A metabolic study was conducted in healthy volunteers. Oral administration of a standard breakfast was consumed during (group B) or 30 min after (group A) the intake of a MCT emulsion (15 g MCT in 70 mL of a 5% aqueous protein solution). Plasma ketones concentration was measured at various time points by a standard enzymatic assay. A control group C received only breakfast.

The Figure illustrates change in plasma ketone average of 15 subjects per group over time for group A, B, and C. Time 0 corresponds to ingestion of the MCT product. Large symbol correspond to time of the ingestion of the breakfast.

TABLE 1

| | Group A | Group B | Group C |
|---|---|---|---|
| Ketones iAUC microM*h | 922 | 600 | 64 |

Table 1 illustrates the incremental AUC obtained for each group. Statistical significant differences ($p < 0.05$) were obtained between group A and B.

These results show that administration of an MCT product before a meal significantly produces larger amount of ketones compared to the same amount of MCT administered during the meal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of increasing production of ketones derived from oral consumption of medium chain triglycerides (MCT) by an individual, the method comprising:
   orally administering to the individual a composition comprising the MCTs; and
   subsequently orally administering to the individual a meal after the orally administering the composition comprising the MCTs, wherein the meal is administered at least about fifteen minutes after the orally administering the composition comprising the MCTs and within about forty minutes after the orally administering the composition comprising the MCTs;
   wherein the composition is administered to the individual in a serving comprising about 15.0 g of the MCTs and the composition comprises the MCTs emulsified in at least one additional component selected from the group consisting of a protein, a lipid, a carbohydrate, and an emulsifier.

2. The method of claim 1, wherein the individual is elderly.

3. The method of claim 1, wherein the composition comprising the MCTs is a liquid.

4. The method of claim 1, wherein the meal is administered about thirty minutes after the orally administering the composition comprising the MCTs.

5. The method of claim 1, wherein the meal is breakfast.

6. The method of claim 1, wherein at least a portion of the MCTs comprises at least one of octanoic acid or decanoic acid.

7. The method of claim 1, wherein at least a portion of the ketones are selected from the group consisting of β-hydroxy butyrate, acetone-acetate and mixtures thereof.

8. The method of claim 1, wherein the production of the ketones in the individual is increased relative to ketone production from orally administering the composition comprising the MCTs and the meal to the individual at approximately the same time.

9. The method of claim 1, wherein the composition is a liquid incomplete nutrition oral nutritional supplement (ONS).

10. The method of claim 1, wherein the individual does not consume any food products other than optional water during a time period starting at the orally administering the composition comprising the MCTs to the individual and ending at the orally administering the meal to the individual.

11. A method of treating a condition for which increased production of ketones from medium chain triglycerides (MCTs) is beneficial, wherein the condition is a neurological condition or a brain energy deficiency condition selected from the group consisting of a migraine, a memory disorder, an age-related memory disorder, a brain injury, a stroke, amyotrophic lateral sclerosis, multiple sclerosis, cognitive impairment, cognitive impairment post-intensive care, age-induced cognition impairment, Alzheimer's disease, Parkinson's disease, Huntington's disease, an inherited metabolic disorder, bipolar disorder, schizophrenia, epilepsy, and combinations thereof, the method comprising:

orally administering, to an individual having the condition or at risk of the condition, a composition comprising the MCTs in a serving or unit dosage form that provides a therapeutically effective amount of the MCTs and/or provides an amount of the MCTs metabolized into a therapeutically effective amount of ketones;

wherein a meal is administered at least about fifteen minutes after the orally administering the composition comprising the MCTs and within about forty minutes after the orally administering the composition comprising the MCTs; and wherein the composition is administered to the individual in a serving comprising about 15.0 g of the MCTs and the composition comprises the MCTs emulsified in at least one additional component selected from the group consisting of a protein, a lipid, a carbohydrate, and an emulsifier.

12. The method of claim 11, wherein the meal is administered about thirty minutes after the orally administering the composition comprising the MCTs.

13. A method of improving or maintaining at least one of neurologic health, cognitive function, or exercise performance in an individual in need thereof, the method comprising:

orally administering to the individual a composition comprising medium chain triglycerides (MCTs); and wherein a meal is administered at least about fifteen minutes after the orally administering the composition comprising the MCTs and within about forty minutes after the orally administering the composition comprising the MCTs;

wherein the composition is administered to the individual in a serving comprising about 15.0 g of the MCTs and the composition comprises the MCTs emulsified in at least one additional component selected from the group consisting of a protein, a lipid, a carbohydrate, and an emulsifier.

14. The method of claim 13, wherein the meal is administered about thirty minutes after the orally administering the composition comprising the MCTs.

* * * * *